US00PP12695P2

(12) United States Plant Patent
Drewlow

(10) Patent No.: US PP12,695 P2
(45) Date of Patent: Jun. 11, 2002

(54) NEW GUINEA IMPATIENS PLANT NAMED 'APPLAUSE ORANGE BLAZE'

(75) Inventor: Lyndon W. Drewlow, Lompoc, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/765,325

(22) Filed: Jan. 22, 2001

(51) Int. Cl.[7] ..... A01H 5/00
(52) U.S. Cl. ..... Plt./318

(58) Field of Search ..... Plt./318

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of New Guinea Impatiens plant named 'Applause Orange Blaze', characterized by its large, bright orange-colored flowers; freely flowering habit with flowers positioned above or beyond the foliage; mounded and compact plant habit; glossy dark green and golden yellow variegated leaves; and tolerance to full sun conditions and low night temperatures.

1 Drawing Sheet

BACKGROUND OF THE INVENTION

The present Invention relates to a new and distinct cultivar of New Guinea Impatiens plant, botanically known as *Impatiens hawkeri,* and hereinafter referred to by the cultivar name Applause Orange Blaze.

The new Impatiens is a product of a planned breeding program Inventor in Lompoc, Calif. The objective of the breeding program is to develop new Impatiens cultivars with compact plant habit and interesting flower and foliage colors.

The new Impatiens originated from a cross made by the Inventor of a proprietary *Impatiens hawkeri* seedling selection designated as code number 91-616-2, not patented, as the female, or seed parent, with a proprietary *Impatiens hawkeri* seedling selection designated as code number 95-568-1, not patented, as the male, or pollen parent. The cultivar Applause Orange Blaze was discovered and selected by the Inventor as a flowering plant within the progeny of the stated cross in controlled environment in Lompoc, Calif.

Asexual reproduction of the new cultivar by terminal cuttings taken at Lompoc, Calif., has shown that the unique features of this new Impatiens are stable and reproduced true to type in successive generations. Plants of the new Impatiens differ from the parent selections primarily in flower and leaf color.

SUMMARY OF THE INVENTION

The following traits have been repeatedly observed and are determined to be the unique characteristics of 'Applause Orange Blaze'. These characteristics in combination distinguish 'Applause Orange Blaze' as a new and distinct Impatiens cultivar:

1. Large, bright orange-colored flowers.
2. Freely flowering habit with flowers positioned above or beyond the foliage.
3. Mounded and compact plant habit.
4. Glossy green and golden yellow variegated leaves.
5. Tolerant to full sun conditions and low night temperatures.

Plants of the new Impatiens can be compared to plants of the cultivar Orange Crush, disclosed in U.S. Plant Pat. No. 10,048. In side-by-side comparisons conducted by the Inventor in Lompoc, Calif., plants of the new Impatiens differ from plants of the cultivar Orange Crush, in the following characteristics:

1. Leaf color of the new Impatiens is variegated whereas leaf color of the cultivar Orange Crush is solid green.
2. Leaves of the new Impatiens have entire margins whereas leaves of the cultivar Orange Crush have serrulate margins.
3. Plants of the new Impatiens have smaller leaves than plants of the cultivar Orange Crush.
4. Plants of the new Impatiens have larger and flatter flowers than plants of the cultivar Orange Crush.
5. Flower color of the new Impatiens and the cultivar Orange Crush differ slightly, 33A and 41A, respectively.
6. Flower spur apices of the new Impatiens are green in color whereas flower spur apices of the cultivar Orange Crush are purple in color.
7. Peduncles of the new Impatiens are lighter in color than peduncles of the cultivar Orange Crush.

Plants of the new Impatiens can also be compared to plants of the cultivar Kisaul, disclosed in U.S. Plant Pat. No. 11,444. In side-by-side comparisons conducted by the Inventor in Lompoc, Calif., plants of the new Impatiens differ from plants of the cultivar Kisaul, in the following characteristics:

1. Leaf color of the new Impatiens is variegated whereas leaf color of the cultivar Kisaul is solid green.
2. Leaves of the new Impatiens have entire margins whereas leaves of the cultivar Kisaul have serrulate margins.
3. Plants of the new Impatiens have smaller leaves than plants of the cultivar Kisaul.
4. Plants of the new Impatiens have larger and flatter flowers than plants of the cultivar Kisaul.
5. Flower color of the new Impatiens is lighter than flower color of the cultivar Kisaul, that is, 33A and 42A, respectively.

6. Peduncles of the new Impatiens are red purple in color whereas peduncles of the cultivar Kisaul are green in color.

BRIEF DESCRIPTION OF THE PHOTOGRAPH

The accompanying colored photograph illustrates the overall appearance of the new cultivar, showing the colors as ture as it is reasonably possible to obtain in colored reproductions of this type. Colors in the photograph may differ slightly from the color values cited in the detailed botanical description which accurately describe the colors of the new Impatiens. The photograph comprises a top perspective view of a typical flowering plant of 'Applause Orange Blaze' grown during the spring in Lompoc, Calif., in a 15-cm container for about 20 weeks after planting a rooted cutting.

DETAILED BOTANICAL DESCRIPTION

The cultivar Applause Orange Blaze has not been observed under all possible environmental conditions. The phenotype may vary somewhat with variations in environment such as temperature, light intensity, daylength, water status and/or fertility level, without, however, any variance in genotype. The following observations and measurements describe plants grown in Lompoc, Calif., during the spring, under commercial practice in a fiberglass-covered greenhouse. Plants used in the following description were grown in 15-cm containers for about 20 weeks after planting rooted cuttings. During the production period, night temperatures were maintained at 16° C. and light levels ranged from 3,000 to 4,000 foot-candles.

In the following description, color references are made to The Royal Horticultural Society Colour Chart except where general terms of ordinary dictionary significance are used.

Botanical classification: *Impatiens hawkeri* cultivar Applause Orange Blaze.

Commercial classification: New Guinea Impatiens cultivar Applause Orange Blaze.

Parentage:

*Female parent.*—Proprietary *Impatiens hawkeri* seedling selection designated as code number 91-616-2, not patented.

*Male parent.*—Proprietary *Impatiens hawkeri* seedling selection designated as code number 95-568-1, not patented.

Propagation:

*Type cutting.*—Terminal cuttings.

*Time to initiate roots.*—Summer: About 8 to 10 days at 23° C. Winter: About 10 to 12 days at 20° C.

*Root description.*—Numerous, fibrous, and freely branching.

Plant description:

*General appearance.*—Mounded and compact plant habit.

*Growth and branching habit.*—Freely branching; pinching, that is, removal of the terminal apices, is typically not required. Vigorous growth habit.

*Foliage description.*—Arrangement: Whorled. Length: About 7 to 8 cm. Width: About 2.5 to 3 cm. Shape: Narrowly ovate to lanceolate. Apex: Acuminate. Base: Acute. Margin: Entire with fine ciliation. Texture: Glabrous. Color: Young foliage, upper surface: 147A, not variegated. Young foliage, lower surface: 183B. Fully expanded foliage, upper surface: Variegated, 147A with 163B along midrib towards leaf base; glossy; venation, red purple. Fully expanded foliage, lower surface: 183C.

Flower description:

*Flower type and flowering habit.*—Single bright orange flowers. Freely flowering, usually about one flower per leaf axil. Flowers positioned above and beyond the foliage and typically face upward or outward. Flowers cupped when opening then mostly flat when opened. Flowers round in shape. Flowers last about two weeks on the plant depending on environmental conditions. Petals self-cleaning; gynoecium persistent. Flowers not fragrant. Flowering indeterminate and continuous.

*Flowering season.*—Year-round under greenhouse conditions. In the garden, flowering from spring until fall.

*Flower diameter.*—About 6 to 6.5 cm.

*Flower buds.*—Rate of opening: From flower bud to fully open flower, typically about 5 to 7 days depending on temperature. Shape: Ellipsoidal.

*Petals.*—Quantity: Single, five per flower, imbricate. Length: Banner petal: About 3 cm. Lateral petals: About 3 cm. Basal or keel petals: About 3.25 cm. Width: Banner petal: About 4 cm. Lateral petals: About 2.5 cm. Basal or keel petals: About 3.5 cm. Shape: Roughly cordate. Apex: Emarginate. Base: Attenuate. Margin: Entire. Texture: Smooth; velvety. Color: Upper surface: 34A; fading to 33A with subsequent development. Lower surface: 33B.

*Spur.*—Length: About 4 cm. Color: 184B.

*Peduncles.*—Length: About 4 cm. Strength: Strong, flexible. Aspect: Mostly upright. Color: 146D overlain with 184D.

*Reproductive organs.*—Androecium: Stamen number: Five fused at anthers, filaments free, hooded. Anther shape: Obovate. Anther color: 34A. Amount of pollen: Moderate. Pollen color: 158D. Gynoecium: Pistil number: One, five-segmented. Stigma color: 185A. Style color: 185A. Ovary length: About 6 mm. Ovary color: 185A.

*Seed development.*—Seed development has not been observed.

Disease resistance: Plants of the new Impatiens have not been observed to be resistant to pathogens common to Impatiens.

Temperature and light tolerance: In Connellsville, Pa., plants of the new Impatiens have been observed to be tolerant to full sun conditions during the summer and to continue to flower. In Lompoc, Calif., plants of the new Impatiens have been observed to be tolerant to low night temperatures about 5 to 10° C. and to continue to flower.

It is claimed:

1. A new and distinct cultivar of New Guinea Impatiens plant named 'Applause Orange Blaze', as illustrated and described.

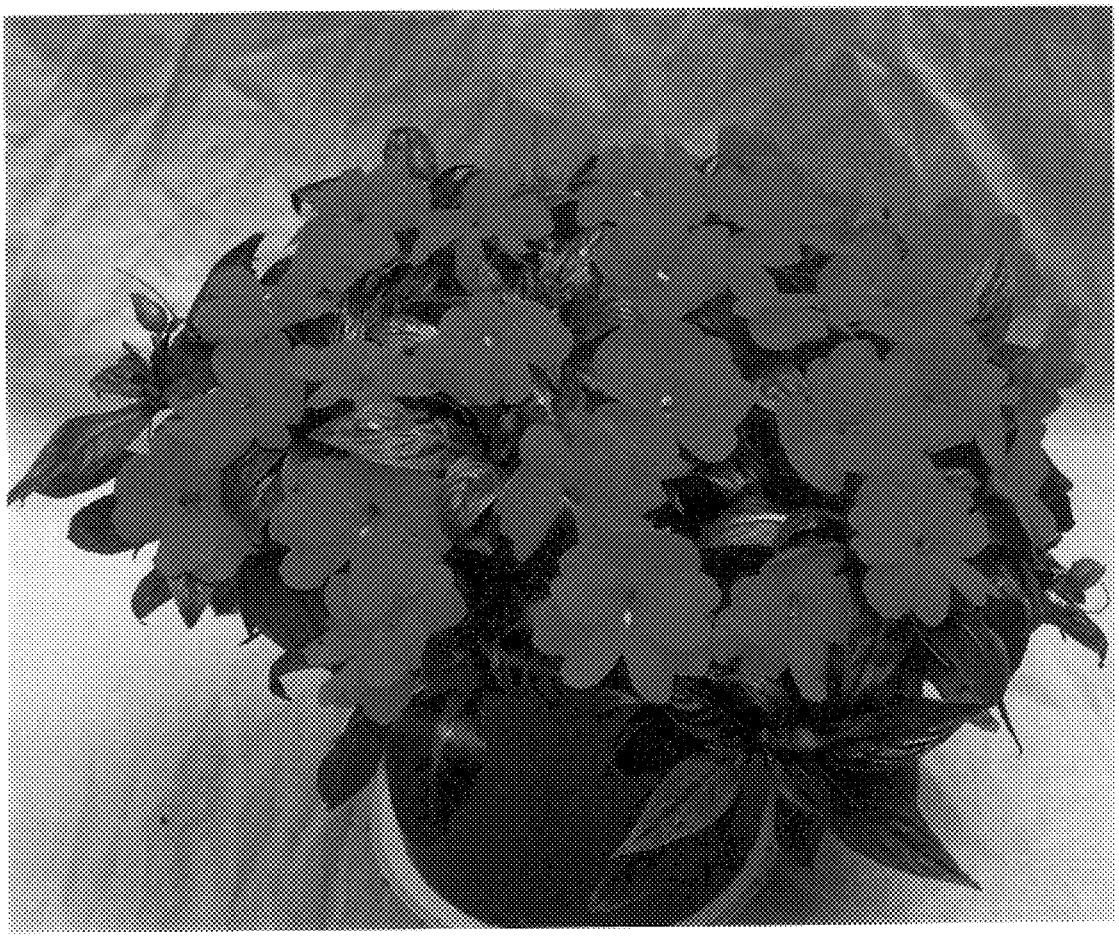

* * * * *